(12) United States Patent
Croisy et al.

(10) Patent No.: US 6,750,368 B2
(45) Date of Patent: Jun. 15, 2004

(54) PROCESS FOR PREPARING SULPHURIC METHACRYLAMIDE AND DEVICE FOR IMPLEMENTING IT

(75) Inventors: Jean-François Croisy, Carling (FR); Michel Tosi, Lixing les St Avold (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/194,891

(22) Filed: Jul. 12, 2002

(65) Prior Publication Data
US 2003/0088123 A1 May 8, 2003

(30) Foreign Application Priority Data
Jul. 13, 2001 (FR) ............................................. 01 09367

(51) Int. Cl.$^7$ ........................ C07C 231/12; C07C 309/02
(52) U.S. Cl. ........................ 562/105; 564/204; 564/124; 564/205

(58) Field of Search ................................. 564/204, 205, 564/112; 562/105

(56) References Cited
FOREIGN PATENT DOCUMENTS

| EP | 0226724 | * | 7/1987 |
| EP | 0999200 A1 | * | 5/2000 |
| GB | 943536 | * | 12/1963 |
| GB | 1186876 | * | 4/1970 |

* cited by examiner

*Primary Examiner*—Shailendra Kumar
(74) *Attorney, Agent, or Firm*—Millen, White, Zelano & Branigan, P.C.

(57) ABSTRACT

The present invention relates to a process for preparing sulphuric methacrylamide. The process can include adding sulphur trioxide and a second part of acetone cyanohydrin without sulfuric add to a reaction medium, after a first part of acetone cyanohydrin with sulphuric acid free of sulfur trioxide is mixed and dehydrated by heating.

17 Claims, 1 Drawing Sheet

PROCESS FOR PREPARING SULPHURIC METHACRYLAMIDE AND DEVICE FOR IMPLEMENTING IT

The present invention relates to a process for preparing sulphuric methacrylamide from acetone cyanohydrin and also to a device for carrying out this process.

Sulphuric methacrylamide or methacrylamide sulphate [$CH_2$=C($CH_3$)—$CONH_2,H_2SO_4$] is an intermediate product which gives methyl methacrylate by reaction with methanol and water.

It is known practice to prepare sulphuric methacrylamide from acetone cyanohydrin and concentrated sulphuric acid.

This preparation generally comprises the reaction of acetone cyanohydrin with concentrated sulphuric acid to give α-hydroxyisobutyramide and α-hydroxyisobutyramide sulphate. These two compounds are then heated to give sulphuric methacrylamide.

Such a preparation is the subject of French patent No. 1 529 440 in which is described a process with staging of the introduction of acetone cyanohydrin, comprising a step in which acetone cyanohydrin is mixed with sulphuric acid using a sulphuric acid/acetone cyanohydrin molar ratio at least equal to 1.5, a step in which the mixture obtained above is subjected to a dehydration by heating, acetone cyanohydrin is then added to the reaction medium so as to again have a sulphuric acid/cyanohydrin molar ratio (of greater than 1) and, finally, the reaction mixture is again subjected to a dehydration by heating.

European patent application No. 226 724 relates to a process for preparing methacrylamide from acetone cyanohydrin and concentrated sulphuric acid, in which a two-phase liquid mixture consisting of an inert, linear, saturated hydrocarbon containing from 5 to 7 carbon atoms and acetone cyanohydrin are introduced into sulphuric acid.

European patent application No. 999 200 relates to apparatus and a process for the high-yielding production of methyl methacrylate or of methacrylic acid, in which a piston-type cracking reactor is used for the thermal conversion.

In the translation of the article published in the Russian journal Zhurnal Prikladnoi Khimii, Vol. 47, No. 6, pp. 1347–1351, June 1974, entitled "Various reactions occurring in the synthesis of methyl methacrylate from acetone cyanohydrin and oleum" by A. A. Michurin, E. A. Sivenkov, E. N. Zil'berman and T. I. Tret'yakova, it is demonstrated that the reaction of acetone cyanohydrin with sulphuric acid to give α-hydroxyisobutyramide sulphate provides better results when it is carried out with a 1/2 cyanohydride/oleum molar ratio in the presence of oleum containing 5 to 10% sulphur trioxide. However, to limit the appearance of side reactions during the subsequent stoving step, it is recommended to work with an oleum containing 0–3% sulphur trioxide.

The aim of the invention is to propose a process for preparing sulphuric methacrylamide which has a high yield even when a small excess of sulphuric acid is used, i.e. when the overall sulphuric acid/acetone cyanohydrin molar ratio is low.

The process according to the invention comprises the following steps:

a) a mixing step, in which acetone cyanohydrin is mixed with sulphuric acid which is free of sulphur trioxide;

b) a stoving step, in which the mixture obtained above is subjected to a dehydration by heating;

c) a step of adding further acetone cyanohydrin, in which more acetone cyanohydrin is added to the reaction medium, without adding more sulphuric acid, and with mixing;

d) another stoving step, in which the mixture is subjected to a further dehydration by heating;

e) optionally, one or more additional step(s) of further addition of acetone cyanohydrin followed by an additional stoving step;

f) optionally, a final stoving step; and it is characterized in that sulphur trioxide is also introduced in step c) and/or just after this step c) and/or, where appropriate, in one or more of the additional steps of further addition e) and/or just after this or these step(s) e).

Such a process thus has the advantage of reducing the number and extent of the side reactions. In addition, it allows the use of starting reagents that are not necessarily anhydrous.

A subject of the invention is also a device for carrying out the process according to the invention.

Other characteristics and advantages of the invention will become apparent on reading the description which follows and which is given with reference to the drawings, in which.

DETAILED DESCRIPTION OF THE INVENTION

Figure 1:
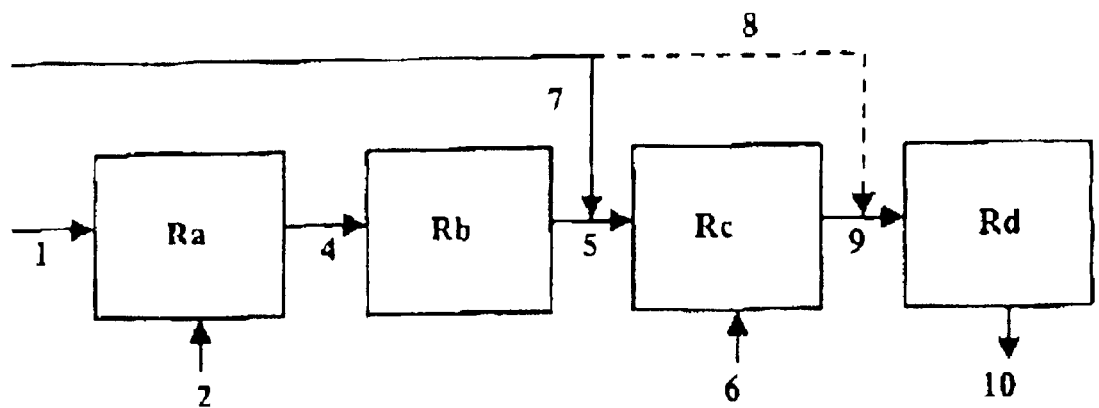
FIG. 1 is a scheme representing the assembly used to carry out the process according to the invention.

The invention is based on the discovery that by introducing sulphur trioxide into points of the process that are already rich in methacrylamide, it is possible to chemically and almost instantaneously convert α-hydroxyisobutyramide into α-hydroxyisobutyramide sulphate, and that the latter is rapidly converted into methacrylamide during a subsequent stoving.

Thus, the introduction of sulphur trioxide may be carried out in step c), i.e. after the pre-stoving step, at which point the sulphuric acid/acetone cyanohydrin molar ratio MR is high, or alternatively just after step c), i.e. at the end of introduction of the acetone cyanohydrin, i.e. when the said molar ratio MR is low.

Preferably, the sulphur trioxide is introduced only in step c).

According to the invention, it is not necessary to work with anhydrous reagents. It is possible to use a sulphuric acid with a titre of close to 100% without targeting a specific titre. In addition, an acetone cyanohydrin of mediocre quality may be satisfactory. It is possible, for example, to use an acetone cyanohydrin containing from 500 to several thousand ppm of water.

The sulphur trioxide may be in the form of oleum, which facilitates its introduction.

The oleum generally contains more than 10% and preferably more than 15% by weight of sulphur trioxide.

It may advantageously correspond to an industrial oleum, for example with a titre of 104.5% ($H_2SO_4$ equivalent—containing about 20% by weight of free sulphur trioxide), obtained on a standard acid regeneration unit of a methyl methacrylate manufacturing process. This is surprising since, in the prior art, especially in the abovementioned Russian publication, the use of an oleum leads to interfering side reactions.

The amount of oleum added is less than 10% by weight relative to the total charge of acetone cyanohydrin and of sulphuric acid. It is preferably between 3% and 5% relative to this total charge.

Thus, such injected oleum contents remain compatible with low molar ratios MR and do not pose any viscosity or crystallization problems, precisely because the oleum is injected after a pre-stoving step, i.e. at a point at which there is already a portion of α-hydroxyisobutyramide sulphate that has been converted into methacrylamide.

Furthermore, no particular exothermicity is produced at the point of injection of the oleum, contrary to the case in the prior art in which the oleum is added directly to the acetone cyanohydrin.

No crystallization is observed either, which would be due to the rise in the content of α-hydroxyisobutyramide sulphate, which conventionally occurs when oleum is injected before the pre-stoving.

According to the invention, the sulphur trioxide is generally injected in slight deficit relative to the α-hydroxyisobutyramide to be converted into α-hydroxyisobutyramide sulphate. This deficit may correspond to a sulphur trioxide/α-hydroxyisobutyramide molar ratio of less than 1 and of the order of 0.8–0.9.

As a result, there is never any free sulphur trioxide in the reaction medium (outlet of step c). This has the advantage of limiting the side reactions associated with the sulphur trioxide, especially the formation of dimethylacrylamide, sultone and polymers.

According to the invention, the molar ratio MR in step c) is generally less than 1.7 and preferably between 1.15 and 1.35.

As regards the assembly to be used to carry out the process according to the invention, it generally comprises, in succession:

a first mixing reactor Ra,
a first stoving reactor Rb,
a second mixing reactor Rc comprising means for introducing acetone cyanohydrin,
a second stoving reactor Rd,
optionally, one or more additional mixing reactor(s) followed by an additional stoving reactor, and
optionally, a final stoving reactor Re, and is distinguished from a conventional assembly in that it also comprises means for introducing sulphur trioxide into reactor Rc and/or at the outlet of this reactor and/or, where appropriate, into one or more of the additional mixing reactors and/or at the outlet of this or these additional reactor(s).

When the assembly comprises additional mixing reactors, each of these reactors is followed by an additional stoving reactor.

FIG. 1 is a diagram illustrating a simplified assembly that may be used to carry out the process according to the invention.

The process according to the invention is generally performed in continuous mode, which may be described as follows.

Sulphuric acid is introduced via line 1, and acetone cyanohydrin via lines 2 and 6. Step a) takes place in reactor Ra.

The mixture obtained in reactor Ra is introduced via line 4 into reactor Rb, where the pre-stoving step b) takes place.

The intermediate product obtained in step b) is then introduced via line 5 into reactor Rc, where it is mixed with fresh acetone cyanohydrin arriving via line 6 and, where appropriate, with oleum arriving via line 7.

The mixture obtained in reactor Rc is then introduced via line 9 into reactor Rd.

Where appropriate, oleum is added via line 8 into the mixture leaving reactor Rc.

The stoving of step d) takes place in reactor Rd.

Where appropriate, reactor Rd may optionally be linked to a final stoving reactor Re.

After the stoving, the methacrylamide sulphate is withdrawn from reactor Rd or, where appropriate, from reactor Re, and is used to manufacture methylmethacrylate or methacrylic acid.

The mixing reactors usually operate at a temperature of between 85 and 105° C. and preferably between 90 and 95° C.

The stoving reactors usually operate at a temperature of between 120 and 145° C. and preferably between 120 and 140° C.

According to one preferred embodiment of the invention, at least one of reactors Rb, Rd and optionally Re is a piston reactor.

EXAMPLES

The examples that follow illustrate the invention without, however, limiting its scope.

All the tests were carried out in an assembly as illustrated in FIG. 1.

The reactor Ra was a stirred jacketed reactor (with a volume of about 270 ml).

Reactor Rb was an electrically heated piston reactor (with a volume of about 60 ml).

Reactor Rc was a stirred jacketed reactor (with a volume of about 300 ml).

Reactor Rd was an electrically heated piston reactor (with a volume of about 36 ml).

A jacketed piston reactor Re (not shown) (with a volume of about 240 ml) was connected to the outlet of reactor Rd.

The main characteristics of the tests were as follows:
the reaction took place continuously over two stages, plus final stoving;
the acetone cyanohydrin was distributed over the two stages (staged feeding with acetone cyanohydrin);
the molar ratio MR was adjusted by varying the amount of acetone cyanohydrin introduced into reactor Rc;
the flow rate of 100% sulphuric acid was kept constant at the inlet of Ra (about 570 g/h) and it was the flow rate of acetone cyanohydrin which was adjusted according to the final MR targeted at the outlet of piston reactor Re;
the sulphuric acid titres were measured by potentiometry (assay with sodium hydroxide);
the contents of formed products were measured by HPLC.

Test 1 (Comparative)

In this test, the ratio MR in reactor Rc was 1.60; the acetone cyanohydrin was distributed in the following manner: 70% in reactor Ra and 30% in reactor Rc.

The other conditions are collated in the following table.

|  | Reactor | | | | |
| --- | --- | --- | --- | --- | --- |
|  | Ra | Rb | Rc | Rd | Re |
| MR | 2.27 |  | 1.6 |  | 1.6 |
| Temperature in ° C. | 90 | 120 | 90 |  | 135 |
| Residence time in min | 38 | 5 | 30 | 2.5 | 24 |

Test 2 (Invention)

In this test, the ratio MR in reactor Rc was 1.50; the acetone cyanohydrin was distributed in the following manner: 70% in reactor Ra and 30% in reactor Rc.

Oleum with a titre of 104.5% was introduced at a rate of 45 g/h via line 7 into reactor Rc.

The other conditions are collated in the following table.

|  | Reactor | | | | |
| --- | --- | --- | --- | --- | --- |
|  | Ra | Rb | Rc | Rd | Re |
| MR | 2.13 |  | 1.5 |  | 1.5 |
| Temperature in ° C. | 90 | 120 | 90 |  | 135 |
| Residence time in min | 38 | 5 | 30 | 2.5 | 24 |

Tests 3 (Comparative), 3a (Invention) and 3b (Invention)

In these tests, the ratio MR in reactor Rc was 1.30; the acetone cyanohydrin was distributed in the following manner: 70% in reactor Ra and 30% in reactor Rc.

In test 3a, oleum with a titre of 104.5% was also introduced at a rate of 45 g/h via line 8 at the outlet of reactor Rc.

In test 3b, oleum with a titre of 104.5% was introduced at a rate of 45 g/h only via line 7 into reactor Rc.

The other conditions are collated in the following table.

|  | Reactor | | | | |
| --- | --- | --- | --- | --- | --- |
|  | Ra | Rb | Rc | Rd | Re |
| MR | 1.84 |  | 1.30 |  | 1.30 |
| Temperature in ° C. | 90 | 120 | 90 |  | 135–140 |
| Residence time in min | 38 | 5 | 30 | 2.5 | 24 |

Tests 4 (Comparative) and 4a (Invention)

In these tests, the ratio MR in reactor Rc was 1.20; the acetone cyanohydrin was distributed in the following manner: 60% in reactor Ra and 40% in reactor Rc.

In test 4a, oleum with a titre of 104.5% was also introduced at a rate of 45 g/h via line 7 into reactor Rc.

The other conditions are collated in the following table.

|  | Reactor | | | | |
| --- | --- | --- | --- | --- | --- |
|  | Ra | Rb | Rc | Rd | Re |
| MR | 1.99 |  | 1.20 |  | 1.20 |
| Temperature in ° C. | 90 | 120 | 95 |  | 140 |
| Residence time in min | 38 | 5 | 30 | 2.5 | 24 |

Tests 5 (Comparative) and 5a (Invention)

In these tests, the ratio MR in reactor Rc was 1.10; the acetone cyanohydrin was distributed in the following manner: 60% in reactor Ra and 40% in reactor Rc.

In test 5a, oleum with a titre of 104.5% was also introduced at a rate of 49 g/h via line 7 into reactor Rc.

The other conditions are collated in the following table.

|  | Reactor | | | | |
| --- | --- | --- | --- | --- | --- |
|  | Ra | Rb | Rc | Rd | Re |
| MR | 1.83 |  | 1.10 |  | 1.10 |
| Temperature in ° C. | 90 | 120 | 95 |  | 140 |
| Residence time in min | 38 | 5 | 30 | 2.5 | 24 |

Results

The methacrylamide yields obtained in all the tests carried out were calculated.

The results are given in the following table.

| Tests | MR | Oleum | % yield |
| --- | --- | --- | --- |
| 1 | 1.60 | no | 91.50 |
| 2 | 1.50 | yes | 92.24 |
| 3 | 1.30 | no | 91.04 |
| 3a | 1.30 | yes | 91.45 |
| 3b | 1.30 | yes | 91.59 |
| 4 | 1.20 | no | 90.05 |
| 4a | 1.20 | yes | 90.34 |
| 5 | 1.10 | no | 87.31 |
| 5a | 1.10 | yes | 87.34 |

Figure 2:
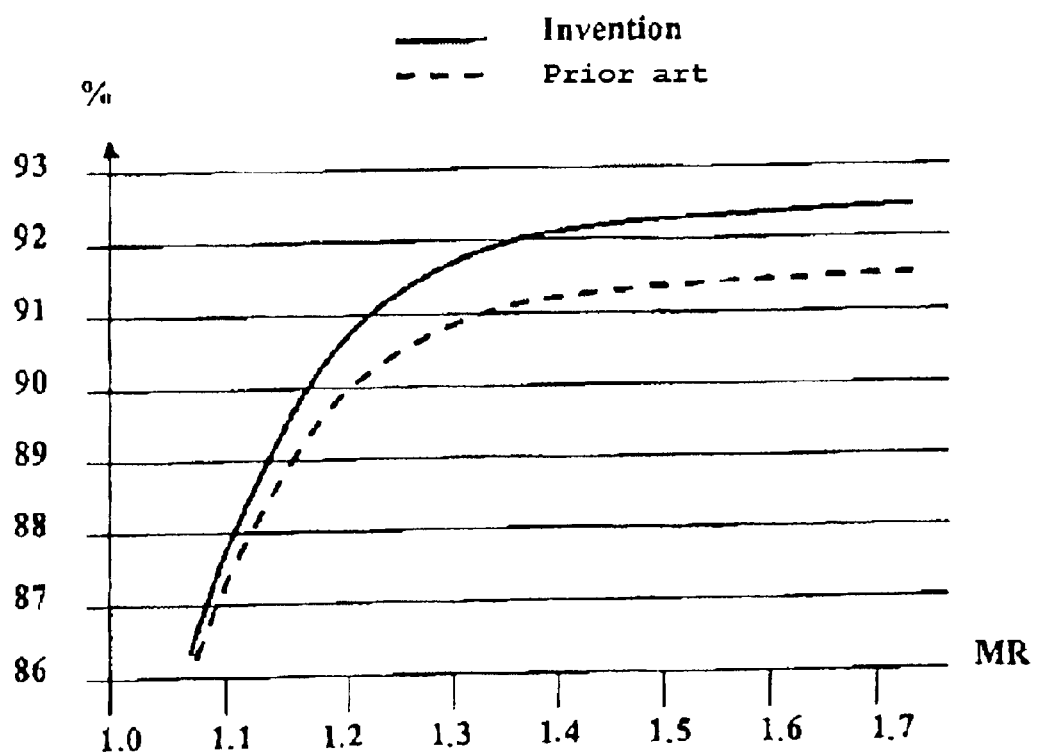
FIG. 2 is a graph representing the change in yield as a function of the sulphuric acid/acetone cyanohydrin molar ratio for the process according to the invention and a process of the prior art.

The curve in FIG. 2 shows the change in yield as a function of the molar ratio MR in reactor Rc.

What is claimed is:

1. A process for preparing sulphuric methacrylamide comprising:
    (a) mixing acetone cyanohydrin with sulphuric acid, which is substantially free of sulphur trioxide, to form a mixture;
    (b) dehydrating the mixture by heating;
    (c) mixing additional acetone cyanohydrin into the mixture without adding more sulphuric acid; and
    (d) further dehydrating the mixture by heating;
    the process further comprising adding sulphur trioxide to the reaction medium during or immediately after (c) or during or immediately before (d).

2. The process of claim 1, further comprising repeating (c) and (d).

3. The process of claim 2, wherein adding sulphur trioxide is performed during or immediately after repeated (c).

4. The process of claim 1, wherein the sulphur trioxide is introduced in the form of oleum.

5. The process of claim 4, wherein the oleum contains more than 10% by weight of sulphur trioxide.

6. The process of claim 4, wherein the amount of oleum added is less then 10% by weight relative to the total charge of acetone cyanohydrin and of sulphuric acid.

7. The process of claim 4, wherein the amount of oleum added is between 3% and 5% relative to the total charge of acetone cyanohydrin and of sulphuric acid.

8. The process of claim 4, wherein the sulphur trioxide is introduced only in (c).

9. The process of claim 1, wherein the sulphuric acid/acetone cyanohydrin molar ratio in (c) is less than 1.7.

10. The process of claim 1, wherein the sulphuric acid/acetone cyanohydrin molar ratio in (c) is between 1.15 and 1.35.

11. The process of claim 1, in which at least one of (b) and (d) are carried out in a piston reactor.

12. The process of claim 1, wherein:
    (a) is performed in a first mixing reactor Ra;
    (b) is performed in a first stoving reactor Rb;

(c) is performed in a second mixing reactor Rc comprising means for introducing acetone cyanohydrin; and (d) is performed in a second stoving reactor Rd.

13. The process of claim 12, wherein at least one of reactors Rb and Rd is a piston reactor.

14. The process of claim 1, further comprising using the sulphuric methacrylamide to manufacture methyl methacrylate.

15. The process of claim 1, further comprising using the sulphuric methacrylamide to manufacture methacrylic acid.

16. The process of claim 4, wherein the oleum contains more than 15% by weight of sulphur trioxide.

17. The process of claim 12, wherein the mixing reactors Ra and Rc operate at a temperature of 85–105° C. and the stoving reactors Rb and Rd operate at a temperature of 120–145° C.

* * * * *

UNITED STATES PATENT AND TRADEMARK OFFICE
CERTIFICATE OF CORRECTION

PATENT NO. : 6,750,368 B2 Page 1 of 1
DATED : June 15, 2004
INVENTOR(S) : Jean-François Croisy It is certified that error appears in the above-identified patent and that said Letters Patent is hereby corrected as shown below:

Column 6,
Line 56, "claim 4" should read -- claim 1 --.

Signed and Sealed this

Twenty-second Day of February, 2005

JON W. DUDAS
*Director of the United States Patent and Trademark Office*